US00PP28889P2

(12) United States Plant Patent
Boomkwekerij

(10) Patent No.: US PP28,889 P2
(45) Date of Patent: Jan. 23, 2018

(54) ***CLEMATIS* PLANT NAMED 'WIT141205'**

(50) Latin Name: ***Clematis koreana* var. *carunculosa***
Varietal Denomination: WIT141205

(71) Applicant: Marco de Wit Boomkwekerij, Boskoop (NL)

(72) Inventor: Marco de Wit Boomkwekerij, Boskoop (NL)

( * ) Notice: Subject to any disclaimer, the term of this patent is extended or adjusted under 35 U.S.C. 154(b) by 0 days.

(21) Appl. No.: 15/330,263

(22) Filed: Aug. 31, 2016

(51) Int. Cl.
*A01H 5/00* (2006.01)

(52) U.S. Cl.
USPC ..... Plt./228

(58) Field of Classification Search
USPC ..... Plt./228
CPC ..... A01H 5/00
See application file for complete search history.

*Primary Examiner* — Kent L Bell
(74) *Attorney, Agent, or Firm* — Penny J. Aguirre

(57) ABSTRACT

A new cultivar of *Clematis* plant named, 'WIT141205' that is characterized by its nodding, semi-double flowers that are light yellow in color tinted brownish purple at the base on outer surface of tepals with staminode centers, its long blooming habit with blooms produced from spring throughout the summer in The Netherlands, and its cold hardiness at least to U.S.D.A. Zone 5.

2 Drawing Sheets

Botanical classification: *Clematis koreana* var. *carunculosa.*

Varietal denomination: 'WIT141205'.

BACKGROUND OF THE INVENTION

The present invention relates to a new and distinct cultivar of *Clematis koreana* var. *carunculosa* (syn. *Clematis chiisanensis*, Atragene Group) and will be referred to hereafter by its cultivar name 'WIT141205'. 'WIT141205' is grown as an herbaceous perennial for landscape use or as a flowering potted plant for the terrace.

'WIT141205' originated as a seedling that arose from seed planted from the open pollination of 'Love Child' (not patented) at the Inventor's nursery in Boskoop, The Netherlands in 2010. 'WIT141205' was selected as a single unique plant in 2011 from amongst the resulting seedlings.

Asexual propagation of the new cultivar was first accomplished by softwood stem cuttings by the Inventor in Boskoop, The Netherlands in 2011. Asexual propagation by softwood stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'WIT141205' as a unique cultivar of *Clematis.*

1. 'WIT141205' exhibits nodding, semi-double flowers with staminode centers.
2. 'WIT141205' exhibits flowers that are light yellow in color tinted brownish purple at the base on outer surface of tepals.
3. 'WIT141205' exhibits a long blooming habit with blooms produced from spring throughout the summer in The Netherlands.

4. 'WIT141205' exhibits cold hardiness at least to U.S.D.A. Zone 5.

The female parent of 'WIT141205', 'Love Child', differs from 'WIT141205' in having single yellow flowers with small spots of brown or purple, and in producing seed. 'WIT141205' can also be compared to the *Clematis* cultivar 'Lemon Bells' (not patented). 'Lemon Bells' is similar to 'WIT141205' in having nodding flowers that are yellow in color. 'Lemon Bells' differs from 'WIT141205' in having single flowers, in having stems that are dark purple in color, and in having ternate leaves with single un-lobed leaflets.

BRIEF DESCRIPTION OF THE DRAWINGS

The accompanying colored photographs illustrate the overall appearance and distinct characteristics of the new *Clematis*. The photographs were taken of a two year-old plant of 'WIT141205' as grown outdoors in a 4.5-liter container in Boskoop, The Netherlands.

The photograph in FIG. 1 provides a side view of the plant habit of 'WIT141205'.

Figure 1:
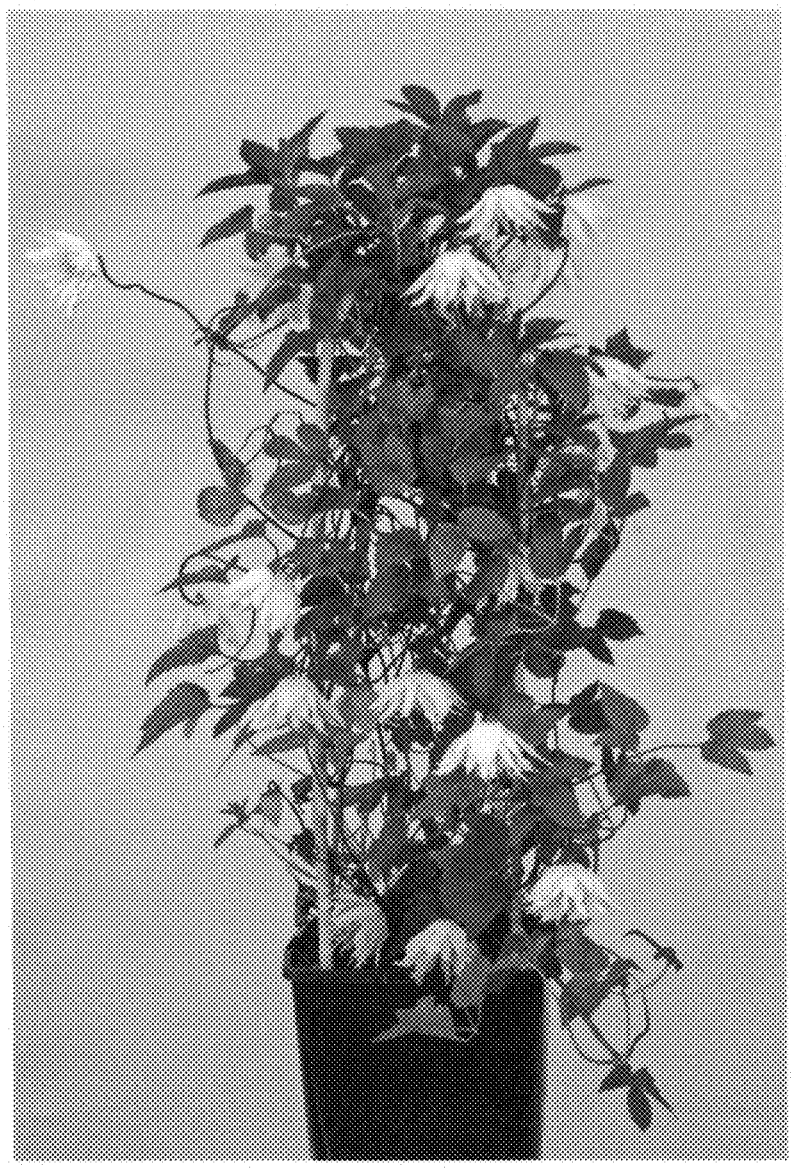
Figure 2:
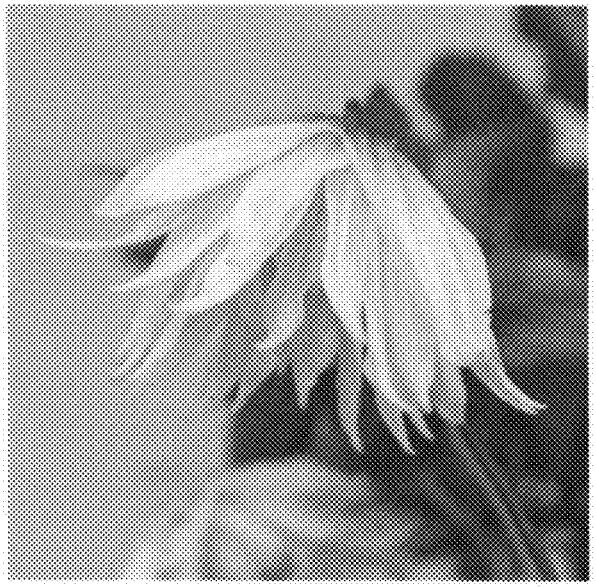

The photograph in FIG. 2 provides a close-up view of a flower of 'WIT141205'.

Figure 3:
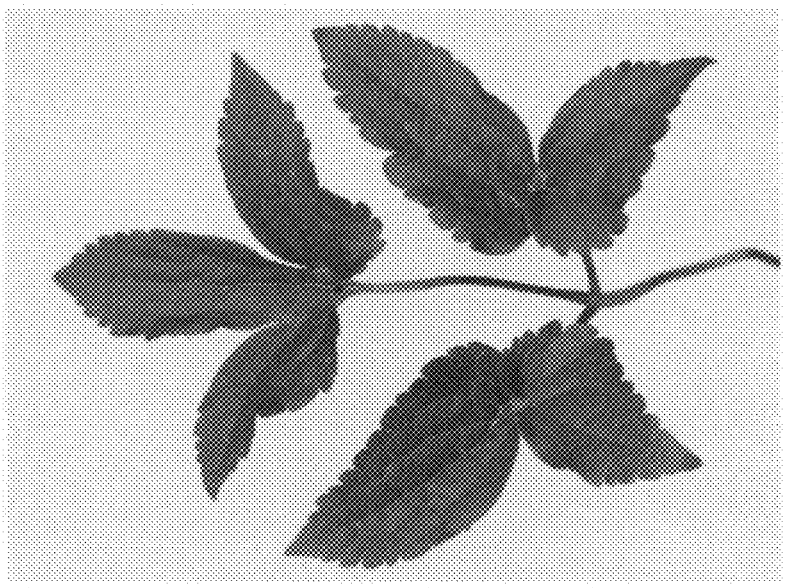

The photograph in FIG. 3 provides a close-up view of a leaf of 'WIT141205'.

The colors in the photographs are as close as possible with the photographic and printing technology utilized and the color values cited in the detailed botanical description accurately describe the colors of the new *Clematis.*

DETAILED BOTANICAL DESCRIPTION

The following is a detailed description of two year-old plants of *Clematis* 'WIT141205' as grown outdoors in 4.5-liter containers in Boskoop, The Netherlands. The phenotype of the new cultivar may vary with variations in environmental, climatic and cultural conditions, as the cultivar has not been tested under all possible environmental conditions. The color determination is in accordance with The 2007 R.H.S. Color Chart, London, England, except where general color terms of ordinary dictionary significance are used.

General description:

*Blooming period*.—Spring, from April or May to July and continues to bloom throughout the summer in The Netherlands, blooming on previous years growth and on new growth.

*Plant type*.—Perennial, deciduous vine.

*Plant habit*.—Herbaceous climber.

*Height and spread*.—An average of 60 cm in height as grown in frame and 90 cm in height as grown without frame, an average of 48 cm in diameter.

*Hardiness*.—At least to U.S.D.A. Zone 5.

*Diseases*.—No susceptibility or resistance to pests and diseases has been observed.

*Root description*.—Fibrous and fine.

*Propagation*.—Softwood stem cuttings.

*Time required for root development*.—An average of six weeks for root initiation with a rooted cutting produced after an average of three to four months.

*Growth rate*.—Moderate to vigorous.

Stem description:

*Shape*.—Rounded to elliptic and slightly 6-ribbed.

*Stem color*.—Young stems upper surface 146A and lower surface 144A, mature stems upper and lower surface 200C to 200D.

*Stem size*.—An average of 74 cm in length and 3 mm in diameter.

*Stem surface*.—Slightly glossy, young stems are moderately to densely pubescent with short hairs an average of 0.6 mm in length and 157D in color.

*Stem aspect*.—Climbing.

*Internode length*.—An average of 12.9 cm, ranges between 6 cm and 20 cm.

*Stem strength*.—Flexible and strong.

*Branching*.—Not freely branched, pinching improves branching and flowering richness, an average of 4 main branches grown from the base with an average of 1 lateral branch per main branch.

Foliage description:

*Leaf arrangement*.—Opposite.

*Leaf quantity*.—An average of 12 (6 pairs).

*Leaf division*.—Compound, 3 leaflets with bi-lobed lateral leaflets and tri-lobed terminal leaflet.

*Leaf size*.—An average of 18.6 cm in length and 11.7 cm in width.

*Leaf shape*.—Ovate in overall shape, with an average of 2 two-lobed lateral leaflets, with lobes ovate in shape, and a three lobed apical leaflet, with lobes ovate in shape.

*Leaf attachment*.—Petiolate.

*Leaf fragrance*.—Fresh "green" fragrance when crushed.

*Leaflet quantity*.—An average of 3 per leaf.

*Leaflet base*.—Oblique or cordate.

*Leaflet apex*.—Acuminate.

*Leaflet venation*.—Pinnate, color; upper surface; a blend between N137B and 146A, lower surface; 146C.

*Leaflet margins*.—Serrate.

*Leaflet attachment*.—Petiolulate.

*Leaflet surface*.—Upper surface; glabrous and very slightly glossy and lower surface; glossy and pubescent, with hairs an average of 0.4 mm in length and 157D in color.

*Leaflet size*.—An average of 5.8 cm in length and width.

*Leaflet color*.—Young upper surface; 144A and lower surface; a blend between 143C and 144B, mature upper surface; a blend between N137B and 146A and lower surface; 146B.

*Petiole*.—An average of 9 cm in length and 2 mm in diameter, 146A in color.

*Petiolule*.—An average of 4.1 cm in length and 1.5 mm in diameter, 144A in color.

Inflorescence description:

*Inflorescence type*.—Solitary, semi-double flowers.

*Inflorescence arrangement*.—Terminal, axillary.

*Peduncle*.—An average of 15.8 cm in length and 2.5 mm in diameter, held straight on top of main stem or at an average angle of 80° to main stem, strong in strength, smooth surface, color; 144A, upper side is suffused with a blend between N186C and 200B toward distal end, lower side is suffused with N199A toward distal end.

*Flower bud*.—Nodding, ovate in shape, an average of 3.1 cm in length and 1.8 cm in diameter, glabrous, fluted surface, color; a blend between 145C, 149D, and 154D, with 145B at the apex.

*Flower fragrance*.—Faint, sweet, and pleasant.

*Lastingness of the flowers*.—Up to 8 days, self-cleaning.

*Flower quantity*.—An average of 3 per lateral stem.

*Flower type*.—Solitary, semi-double.

*Flower shape*.—Campanulate with rotate tepals and tepal-like staminodes.

*Flower aspect*.—Nodding.

*Flower size*.—An average of 7.5 cm in diameter and 4.2 cm in depth.

*Tepals*.—An average of 4, cruciform, narrow ovate shape, acute apex, entire margin, fused base, upper and lower surfaces glabrous, dull, and fluted, an average of 5 cm in length and 2 cm in width, color; upper and lower surface when opening; 4D with apex 4C to 4D and base of lower surface 145B, upper surface when fully opened; 4C to 4D and lower surface; 10D, base suffused with 177A to 177B, color fades to 1C suffused with 199C.

*Staminodes*.—An average of 85, rotate in multiple rows forming semi-double flowers, narrow lanceolate to narrow elliptic in shape, acute apex, cuneate base, entire margin, upper and lower surfaces glabrous, full, and fluted, an average of 3.4 cm in length and 6 mm in width with outer staminodes an average of 4.6 cm in length and 9 mm in width and inner staminodes an average of 1.8 cm in length and 2 mm in width, color; 4D with apex 4C to 4D, inner staminode apex is 1B.

Reproductive organs:

*Gynoecium*.—Numerous pistils, up to about 150, an average of 1 cm in length, stigma; narrow, club-shaped, and curved in shape, 145D in color, style; 9 mm in length and 145B to 145C in color, ovary; 145B in color.

*Androecium*.—No stamens present, all staminodes.

*Fruit and seed*.—Seed heads have not been observed to date.

It is claimed:

1. A new and distinct cultivar of *Clematis* plant named 'WIT141205' as herein illustrated and described.

* * * * *